United States Patent [19]

Vorosmarthy

[11] Patent Number: 4,976,732
[45] Date of Patent: Dec. 11, 1990

[54] OPTICAL LENS FOR THE HUMAN EYE
[75] Inventor: Vorosmarthy, Los Angeles, Calif.
[73] Assignee: International Financial Associates Holdings, Inc., Beverly Hills, Calif.
[21] Appl. No.: 649,909
[22] Filed: Sep. 12, 1984
[51] Int. Cl.⁵ ............................................. A61F 2/16
[52] U.S. Cl. ......................................................... 623/6
[58] Field of Search ............................................. 623/6
[56] References Cited

U.S. PATENT DOCUMENTS

| 3,034,403 | 5/1962 | Neefe | 623/6 |
|---|---|---|---|
| 3,270,099 | 8/1966 | Camp | 623/6 |
| 4,010,496 | 3/1977 | Neefe | 623/6 |
| 4,402,579 | 9/1983 | Poler | 623/6 |

Primary Examiner—V. Millen
Attorney, Agent, or Firm—Daniel J. Meaney, Jr.

[57] ABSTRACT

An optical lens adapted for use with a human eye having a lens body formed of a top surface and a bottom surface and wherein the lens body has integral therewith a predetermined area which is adapted to selectively intercept and pass light through the lens body in a manner to obtain an optical effect for substitution of the loss of the accommodation of a phakic, aphakic and pseudophakic eye is shown. The optical lens may be used in an intraocular lens configuration having resilient support means operatively coupled to the lens body adapted to slidably engage tissue in the chamber of an eye to position the lens body in a proper optical relationship. Also, the optical lens can be placed over the cornea of the eye or in the cornea directly by a cornea inlay.

18 Claims, 4 Drawing Sheets

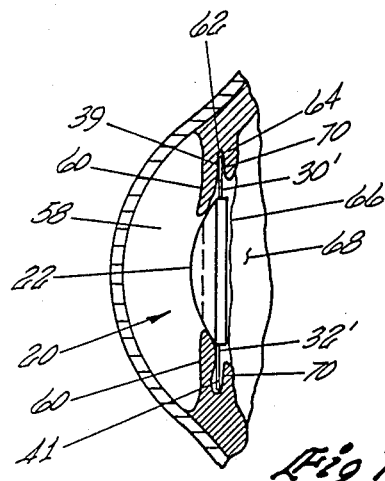
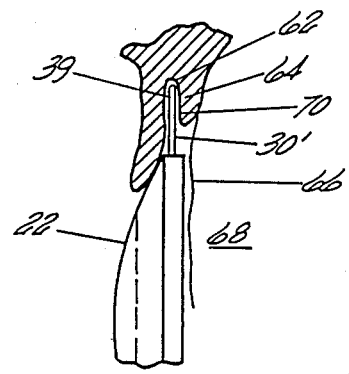
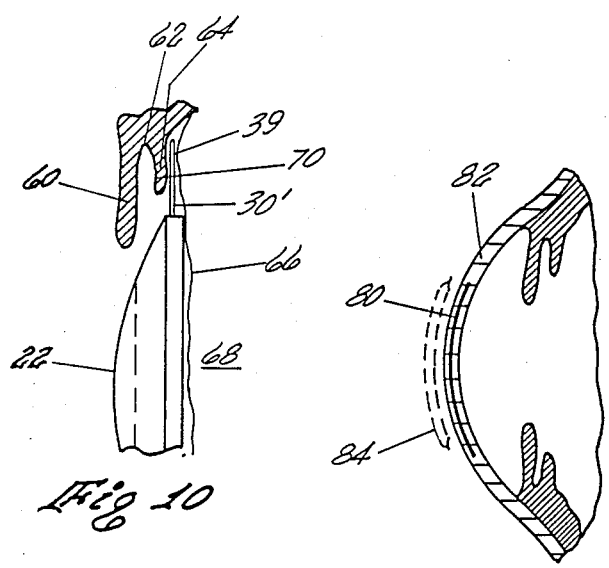
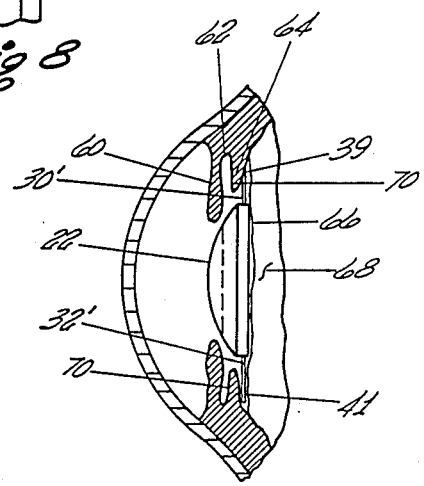
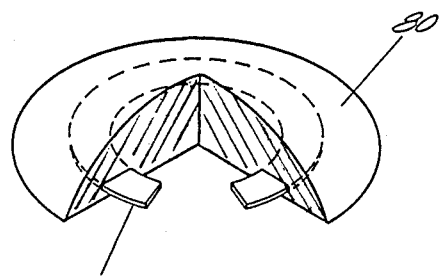

OPTICAL LENS FOR THE HUMAN EYE

BACKGROUND OF THE INVENTION

1. Field of the Invention

This invention relates to an optical lens for a phakic, aphakic and pseudophakic eye and more specifically relates to an optical lens which is adapted to be inserted into the eye or used in conjunction with an intraocular lens to restore the loss of near and far accommodation of the eye. Also, the teachings of this invention can be used in a contact lens located on the surface of an eye.

2. Description of the Prior Art

Intraocular lenses adapted to be implanted into an eye are well known in the art. Typical of such intraocular lenses are the lenses described in U.S. Pat. No. 4,159,546 to Shearing; U.S. Pat. No. 4,249,271 to Polar; and U.S. Pat. No. 4,244,060 to Hoffer. Another known intraocular lens which is adapted to be implanted in either the anterior chamber or posterior chamber of an eye is a Universal Intraocular Lens invented by Dennis D. Shepard, M.D., F.A.C.S. In one embodiment of the Universal Intraocular Lens of Dr. Shepard, the lens element is formed into a plano-convex lens and has four resilient support members which deflect and move within the plane of the lens body relative to the pupil in a proper optical relationship.

It is also known to insert a lens directly into the cornea of the eye, by means of a cornea inlay, in a phakic, aphakic and pseudophakic eye.

It is also known in the art to use a tinting material in contact lenses for the purpose of appearance only, which has no optical effect. Contact lenses are known which utilize different refractive indexes to form a bifocal lens element. However, the position of the iris is an important part of the bifocal operation

SUMMARY OF THE INVENTION

The present invention relates to a new and novel optical lens for an eye which is adapted to be implanted directly into the eye and which can be implanted into either the anterior or posterior chamber of an eye. Also, the optical lens can be utilized in cooperation with an artificial intraocular lens. In the alternative, the lens body can be fabricated to be placed either on the surface of the cornea or used in a cornea inlay. The optical lens device functions to restore the loss of near and far accommodation of the eye. In the preferred embodiment, the optical lens for an eye includes a lens body which has a top surface and a bottom surface. The lens body is formed in the center area to have a predetermined area which is adapted to selectively intercept and pass light through the lens body. The light passes through the lens body in a manner to obtain an optical effect for substitution of the loss of the accommodation of the eye. In addition, the optical lens can be formed with a resilient support means which is operatively coupled to the lens body and adapted to engage tissue in the chamber of an eye to position the lens body in a proper optical relationship to the pupil.

None of the known prior art intraocular lenses are adapted to provide an optical effect for substitution of the loss of the accommodation of the eye.

One advantage of the present invention is that the optical effect of substitution for loss of the accommodation of the eye can be accomplished by increasing the normal depth of focus of the eye by means of the effect of an intraocular stenopaeic hole.

A further advantage of the present invention is that the optical lens can obtain the optical effect by providing different refractive powers to the different parts of the lens body.

Another advantage of the present invention is that an optical lens can be formed in a similar manner to that of an intraocular lens, the surface of the lens can be fabricated to have a differential refractive power, and the central area of the lens can be formed of an opaque material which defines an intraocular stenopaeic hole of a selected diameter.

A yet further advantage of the optical lens of the present invention is that, in the case of distance vision, the pupil is partially subjected to ambient illumination so as to permit the light rays to enter the peripheral part of the intraocular lens body as well as through the stenopaeic hole, and such a lens permits an eye to adapt to darkness.

A still further advantage of the present invention is that the central area of the lens body can be fabricated from any suitable opaque material, such as silver, plastic, or laminated thin layers of material. Also, it is envisioned that the material could be completely encapsulated within the intraocular lens body in order to achieve the optical effect. Also, the opaque material can be placed on either the top surface or the bottom surface of a lens body.

BRIEF DESCRIPTION OF THE DRAWINGS

The foregoing and other advantages of this invention will be apparent from the following description of the preferred embodiment of the invention when considered with the illustrations and accompanying drawings which include the following figures:

FIG. 7 is a diagrammatic representation of the implantation of an optical lens of the present invention implanted in the posterior chamber of an eye and located between the iris and the ciliary processes;

FIG. 8 is a partial end plan view portion in cross section showing the location of the optical lens and the resilient support means between the iris and the ciliary processes;

FIG. 9 is a pictorial representation showing the optical lens of the present invention implanted in the lens capsular bag between the ciliary processes and the end of the hyaloid membrane and/or posterior lens capsule;

FIG. 10 is a partial end plan view in cross section showing the relationship between the resilient support means of the optical device located among the ciliary processes, the lens capsular bag, and the end of the hyaloid membrane and/or posterior lens capsule;

FIG. 11 is a pictorial representation showing a different embodiment of the optical lens in a cornea inlay;

FIG. 12 is a pictorial representation of an optical lens used in FIG. 11;

DESCRIPTION OF THE PREFERRED EMBODIMENT

Figure 1:
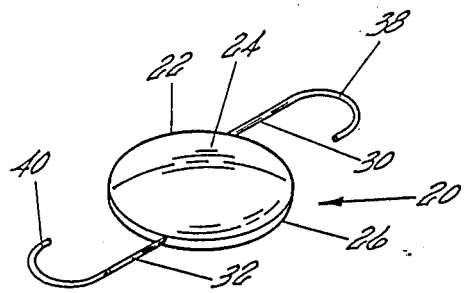
FIG. 1 is a perspective view of an optical lens, having "J" loop strands, which utilizes the present invention.
Figure 3:
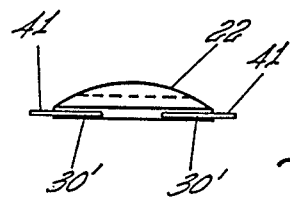
FIG. 3 is a top plan view of an optical lens of the present invention.
Figure 5:
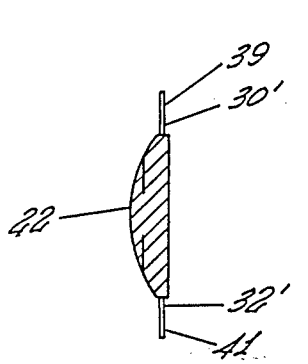
FIG. 5 is a cross section taken along section lines 5—5 of FIG. 2.
Figure 2:
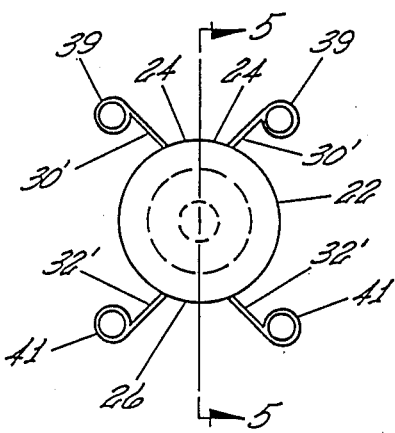
FIG. 2 is a front view of a different embodiment of an optical lens utilizing the present invention.
Figure 4:
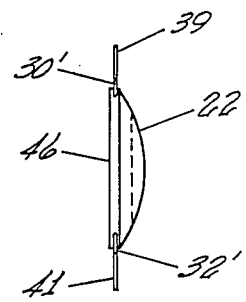
FIG. 4 is a right side plan view of an optical lens of the embodiment of FIG. 2.

Before commencing the detailed description of the preferred embodiment, the following background is provided. The concept of the present invention is to utilize an optical lens which is adapted to be used in a human eye by being placed over the cornea, in a cornea inlay, or as an integral part of an intraocular lens which is implanted into an eye. The location of the lens would be determined by the surgeon, as is well known in the art. The optical lens is able to restore the loss of near and far accommodation of the eye.

In order to obtain the optical effect of substitution for the loss of the accommodation of the eye, the optical effect can be accomplished in two ways. First, the lens can have the lens body thereof specifically designed in a manner so as to increase the normal depth of focus of the eye by means of the effect of an intraocular stenopaeic hole. A second way is to design and fabricate the lens body in a manner such that the lens body has predetermined selected different refractive characteristics or powers so that the transmitted light is deflected in a manner determined by the characteristics of that portion of the lens body which transmits the light. Also, the optical effect can be obtained by combining each of the above into a single optical lens.

In utilizing the technique of increasing the normal depth of focus of the eye by means of the effect of an intraocular stenopaeic hole, the depth of focus of the eye must be increased by the optical lens until the focus point reaches or surpasses the reading distance of the human eye. Typically, this range is in the order of about 20 centimeters to about 35 centimeters.

The desired optical effect to restore the near accommodation of a distance-corrected eye can be achieved by controlling the diameter of the stenopaeic pinhole. The typical range for distance of the posterior focus of the eye has a mean average distance of approximately 22 millimeters. The diameter of the stenopaeic pinhole would range in the order of 0.05 millimeters to about 2.00 millimeters, depending on the changes of the physiological and optical conditions of the eye and its illumination. The stenopaeic pinhole is created in the center of the lens body by an opaque area creating an artificial iris diaphragm. This is illustrated in FIGS. 1 through 6 and FIGS. 13, 14 and 15. The external diameter of the diaphragm, when measured in relation to the diameter of the pupil of the eye, is generally in the order of 2.00 millimeters to about 5.00 millimeters and is smaller than the pupil of an eye. Selecting the external dimension of the diaphragm such that the external dimension thereof is less than the pupil permits the light rays to pass through the peripheral annular part of the lens body and past the opaque center area to obtain the far accommodation effect.

Although both of the above-described techniques can be utilized, the physiological movement of the pupil makes the use of the optical effect of the stenopaeic pinhole diaphragm optic lens preferable in most applications.

Referring now to FIG. 1, the optical lens illustrated therein is adapted to be implanted into the human eye. The optical lens 20 includes a lens body 22 having a top surface 24 and a bottom surface 26. In the illustration of FIG. 1, the basic form of the lens body is a plano-convex lens. The lens body 22 has an internal center area formed of an opaque material to selectively intercept and pass light. In the embodiment of FIG. 1, the lens is shown in the form of an intraocular lens having a resilient support means, such as "J" loop support means 30 and 32. Each "J" loop strand has one end thereof secured into the periphery of the lens body 22 and the other end thereof, such as ends 38 and 40 of "J" loop strands 30 and 32, respectively.

FIGS. 2 through 5 illustrate another embodiment of an intraocular lens utilizing an interior, endless annular-shaped opaque member wherein the resilient support means comprise four strands 30' and 32' formed into circular elements 39 and 41. The lens body utilizes the embedded annular loop of opaque material to obtain the optical effect by increasing the normal depth of focus of the eye by means of the effect of an intraocular stenopaeic hole.

Figure 6:
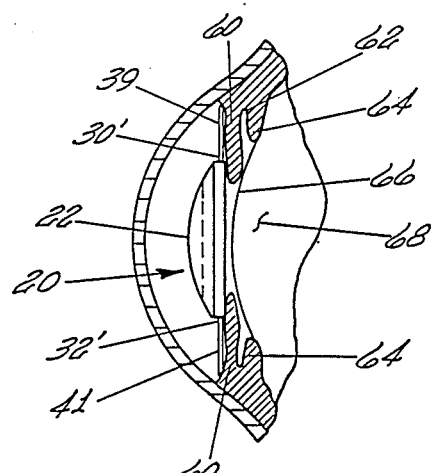
FIG. 6 is an illustration of an implantation of the optical lens of FIG. 2 in the anterior chamber of an eye.

FIG. 6 illustrates the implantation of the optical lens 20 into the anterior chamber of the eye. The resilient support members 30' and 32' are located adjacent to iris 60 of the eye. Behind the optical lens 22 is the hyaloid membrane 66 which maintains the vitreous humor 68 within the eye. The iris 60 and the ciliary processes 64 define the iridiocapsular cleft 62 which is located in the posterior chamber of the eye.

FIG. 7 and FIG. 8 illustrate the implantation of the optical lens 20, utilizing this invention, in the posterior chamber of the eye. Typically, the resilient support means 30' and 32' and their associated annular-shaped guide and support elements 39 and 41, respectively, are located in the iridiocapsular cleft 62 which is located between the iris 60 and the ciliary processes 64. The hyaloid membrane 66 has an end 70 which is attached to the ciliary processes 64.

In FIG. 9, the optical lens 20, utilizing the teachings of this invention, is positioned within the posterior chamber such that the lens body thereof is centered within the pupil. The iris 60 and the ciliary processes 64 support the support element 39 located at one end of the resilient support means 30' therebetween. The hyaloid membrane 66 extends behind the optical lens 22.

FIG. 10 shows in greater detail the support element 39 of the optical lens 20 positioned within the iridiocapsular cleft 62 located between the iris 60 and the ciliary processes 64.

FIG. 11 illustrates the use of an optical lens 80 which has been implanted into the cornea 82 in a cornea inlay.

Alternatively, the optical lens 80 can be placed over the cornea in the position shown by dashed lens 84.

FIG. 12 is a pictorial representation of the optical lens 80 having a ring 86 embedded within the lens body. This enables a contact lens to obtain the optical effect for substitution of the loss of the accommodation of an eye by increasing the normal depth of focus of the eye by means of the effect of an intraocular stenopaeic hole.

Figure 13:
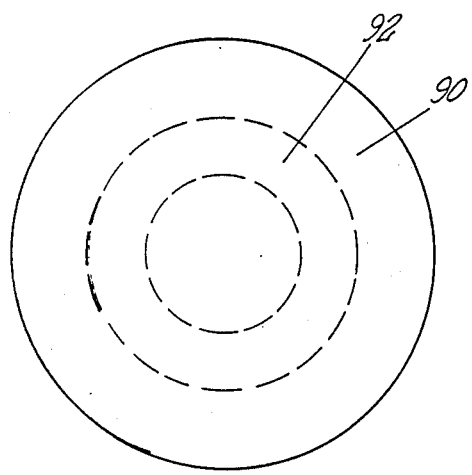
FIG. 13 is a front plan view of a lens having an endless annular loop formed of an opaque material located interior of the lens body.
Figure 14:
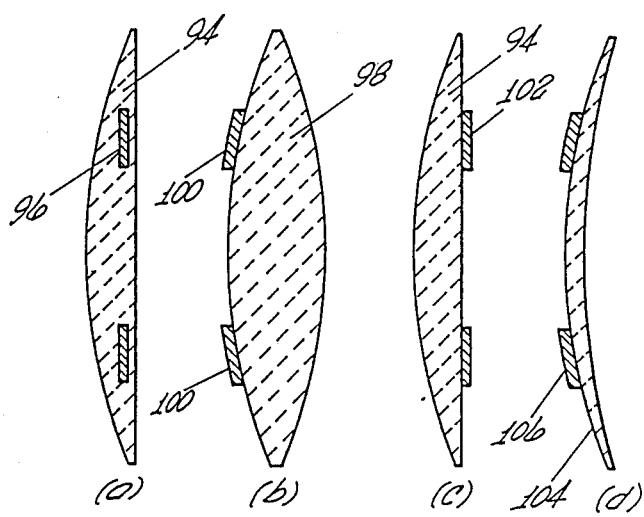
FIGS. 14(a), 14(b), 14(c) and 14(d) are four different cross-sectional shapes of lenses having the opaque area located at different locations on the lens body to form a single stenopaeic pinhole in the lens body.

FIG. 13 illustrates that the optical lens functions as an iris diaphragm and can have a wide range of shapes and locations for the opaque ring. In FIG. 13, the lens body 90 has the endless annular-shaped member formed interiorly therein, and the stenopaeic pinhole effect is created in the center by the non-transparent or opaque disc 92. Thus, the embodiment of FIG. 13 can be characterized as an artificial iris diaphragm. The external dimension of the lens body 90 of FIG. 13 is about 6.00 millimeters. The annular-shaped member 92 located within the lens body 90 has an outside diameter of about 3.50 millimeters, but this diameter can be anywhere between about 2.00 millimeters to about 5.00 millimeters. The annular-shaped member 92 has an inside dimension to define the stenopaeic in the order of about 0.75 millimeters, but this can vary between about 0.05 millimeters to about 2.00 millimeters. It is preferable to have the external dimension of the lens body less than the diameter of the pupil of the eye. Also, a difference in the dimension of the diameter between the lens body and the diameter of the outside of the mid-width dilation pupil is required to enable the light rays to pass through the peripheral annular part of the lens body to obtain the far accommodation.

FIG. 14(a) illustrates, in cross section, that a plano-convex lens body 94 has the annular member 96 formed in the center thereof and that the stenopaeic pinhole defining the light transmission path extends from the top surface, through the lens body, and out the bottom surface.

FIG. 14(b) illustrates a bi-convex lens wherein the top surface of the lens body 98 has an annular-shaped member of opaque material 100 formed on the surface thereof to provide the stenopaeic pinhole effect.

FIG 14(c) shows an alternate embodiment of a plano-convex lens body 94 having an annular-shaped member 92 formed on the bottom thereof to provide the stenopaeic pinhole effect.

FIG. 14(d) shows a meniscus lens body 104 having an annular-shaped member 106 formed on the bottom surface thereof to form the stenopaeic pinhole effect. Any of the lens bodies in FIGS. 14(a), 14(b), 14(c) and 14(d) can have the opaque annular member located on the top surface, in the lens interior, or on the bottom surface.

Figure 15:
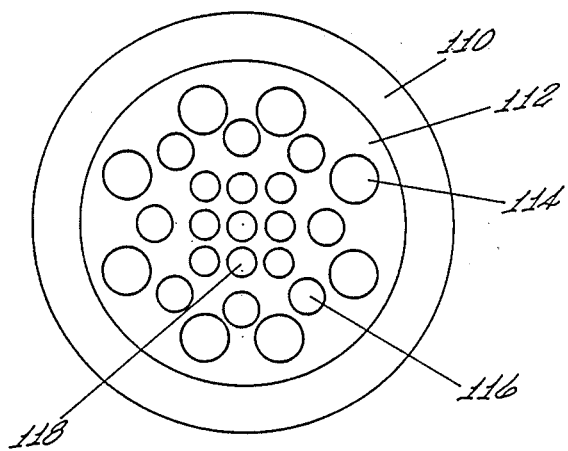
FIG. 15 is a diagrammatic representation of an optical lens having multiple stenopaeic pinholes.

FIG. 15 illustrates an alternate embodiment for a lens body 110 of an optical lens of the present invention. In the event that the lens device cannot be exactly centered in the eye, the lens body 110 has positioned in the center thereof a fairly large disc-shaped member 112 formed of an opaque material, and the disc 112 has a plurality of, or multiple, apertures formed therein which are shown generally as 114, 116 and 118. The apertures 114, 116 and 118 are positioned in a predetermined pattern so that each of the apertures is axially aligned in a spaced relationship with each other and each of the apertures has a predetermined diameter. Rather than using a disc with holes, a grid formed of opaque material with preselected hole sizes could be used to achieve the same effect. With the embodiment of FIG. 15, the combination of apertures provides the desired stenopaeic pinhole effect and the optical lens of FIG. 13 allows a continuous form of accommodation and adaptation of the eye.

Figures 16A, 16B:
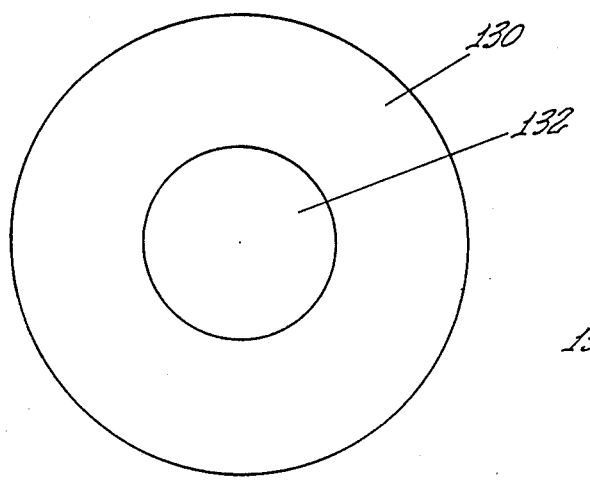
FIGS. 16(a) and 16(b) are illustrations of another embodiment of an optical lens of the present invention formed to have different refractive indexes at the center and edge thereof.

FIG. 16(a) illustrates an embodiment for providing the optical effect by use of a difference in refractive power of the lens material. In FIGS. 16(a) and 16(b), the basic lens body is a plano-convex lens 130. The center of the convex surface is formed of an arcuate-shaped central area 132. The difference in refractive characteristics of the plano-convex section 130 and the arcuate-shaped central member 132 functions to restore the loss of near and far accommodation of the eye. In the embodiment of FIGS. 16(a) and 16(b), the plano-convex section 130 has a refractive power of about +1.00 to about +3.00 diopters relative to the center of the lens body having the central area 132 formed thereon. The central area 132 would have an external dimension in the order of about 1.00 to about 3.00 millimeters in diameter. The optical lens described in FIGS. 16(a) and 16(b) is usable during constriction of the principal, as occurs during near work and with adequate illumination.

As noted above, it is possible to combine the stenopaeic pinhole effect illustrated in FIG. 13 with the differential refractive characteristic of the lens body illustrated in FIGS. 16(a) and 16(b).

Figures 17, 18:
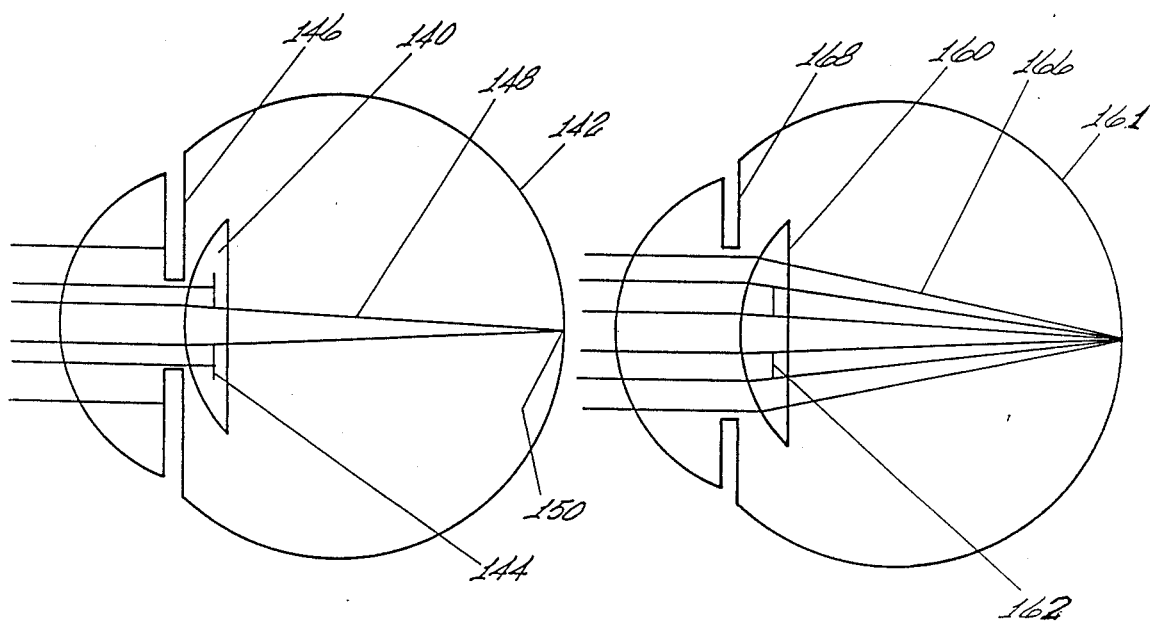
FIG. 17 is a diagrammatic representation of the optical effect of an optical lens which is partially covered by the iris and which increases the normal depth of focus of an eye.
FIG. 18 is a diagrammatic representation of an optical lens, having different refractive powers, which is uncovered by the iris for focusing the transmitted light.

FIG. 17 illustrates graphically the position of an optical lens 140 within an eye 142 wherein the optical lens 140 has an internal opaque ring 144 which provides the stenopaeic pinhole effect. The iris 146 partially covers the lens body 140. The internal opaque ring 144 receives rays of light 148 and focuses the same at a focus point 150. The optical lens 140 controls the depth of the focus in order to restore the loss of near and far accommodation of the eye. In the case of near vision, the eyes converge and the pupils narrow. The pupillary constriction (miosis) is increased by the excess illumination which is available at a normal reading distance. Thus, in the case of near vision utilizing the optical lens 140 of FIG. 17, the peripheral part of the optical lens is covered by the iris 146. Only the central part of the optical lens having the annular ring 144 gives a sharp, focused sight for near vision.

FIG. 18 illustrates an embodiment of an optic lens 160 which is located within an eye 161. The optic lens 160 utilizes both the refractive charactistic of the periphery of the lens body and the annular-shaped member 162 to pass the rays of light 166 through the optical lens 160. The iris 168 is removed from the optical lens 160 as shown, resulting in more light passing through the entire lens body 160. In the illustration of FIG. 18, in the case of distant vision with ambient illumination, the pupil is in a mid-width dilation state and permits the light rays to enter the peripheral part of the optical lens as illustrated by light rays 166 of FIG. 18. This permits the light rays 166 to enter the peripheral part of the optical lens 160 as well as through the center of the annular-shaped member and permits adaptation to darkness.

The lens body for practicing the invention can be fabricated from any suitable lens material. The opaque or non-transparent member can be formed of such material as silver, plastic or a paint layer, if that material is completely enclosed in the optical lens. Preferably, the optical lens can be fabricated from a bio-compatible material, such as platinum, platinum iridium, gold, stainless steel, suitable paint or tinted material or appropriate approved plastic.

What is claimed is:

1. An optical lens for a human eye comprising
a lens body having a top surface and a bottom surface, said lens body having formed in the center area thereof a predetermined area of opaque material defining a ring-like annular-shaped member which is adapted to selectively intercept and pass light through the lens body along a predetermined light transmitting path in a manner to obtain an optical effect for substitution of the loss of the accommodation of an eye.

2. The optical lens of claim 1 further comprising
resilient support means operatively coupled to said lens body and adapted to engage tissue in the chamber of an eye to position the lens body in a proper optical relationship to the pupil.

3. The optical lens of claim 2 wherein said lens body obtains the optical effect by providing different refractive powers to selected parts of an intraocular lens body.

4. The optical lens of claim 1 wherein said ring-like predetermined area is an endless loop.

5. The optical lens of claim 1 wherein said lens body is a plano-convex lens.

6. The optical lens of claim 1 wherein said lens body is a bi-convex lens.

7. The optical lens of claim 1 wherein said lens body is a meniscus lens.

8. An optical lens for the human eye adapted to be placed over the cornea of an eye comprising:
a lens body having a top surface and a bottom surface, said lens body having positioned in the center area thereof a predetermined area formed of an opaque material which is adapted to selectively intercept and pass light through the lens body along a predetermined light transmitting path in a manner to obtain the optical effect by increasing the normal depth of focus of the eye by means of the effect of an intraocular stenopaeic hole.

9. In combination
an optical lens adapted to be implanted into an eye positioned in at least one of the anterior chamber and posterior chamber of the human eye, said optical lens comprising
a lens body having a top surface and a bottom surface, said lens body being formed of an opaque material defining an annular-shaped member which is adapted to selectively interrupt and pass light through the lens body in a manner to obtain an optical effect for substitution of the loss of accommodation of an eye; and
resilient support means operatively coupled to said lens body and adapted to engage tissue in the chamber of an eye to position the lens body in a proper optical relationship to the subject.

10. The combination of claim 9 wherein said optical lens body provides the optical effect by increasing the normal depth of focus of the eye by means of the effect of an intraocular stenopaeic hole having a predetermined geometric dimension which is less than the geometric dimension of the pupil of an eye.

11. The combination of claim 9 wherein said lens body includes means for providing the optical effect by providing different refractive powers to selected parts of an intraocular lens body.

12. An intraocular lens for a human eye comprising
a lens body having a top surface, a bottom surface, a central area which is capable of transmitting light determined by the characteristic of that portion of the lens body and a peripheral area surrounding said central area which defines a ring-like annular-shaped member formed of an opaque material.

13. The intraocular lens of claim 12 wherein said peripheral area is a layer of light blocking material coated on the top surface of the lens body around said central area.

14. The intraocular lens of claim 12 wherein said lens body has the peripheral area integral with the central area and the peripheral is formed of a different material having different light transmittance characteristic than material defining the central area.

15. An optical lens for a human eye comprising
a lens body having a top surface and a bottom surface, said lens body having formed in the central area thereof a predetermined area of material which is adapted to selectively interrupt and pass light through the lens body along a predetermined light transmitting path in a manner to obtain an optical effect for substitution of the loss of accommodation of an eye, said lens body obtaining said optical effect by increasing the normal depth of focus of the eye by means of the effect of an intraocular stenopaeic hole.

16. The optical lens of claim 15 wherein the predetermined area is shaped into an endless annular member formed of an opaque material and the center of the endless annular member defines a light transmitting path extending axially through the top surface, through the lens body and through the bottom surface.

17. The optical lens of claim 15 wherein said opaque area defines a plurality of axially aligned, spaced light transmitting paths each having a selected cross-sectional area extending through the lens body.

18. The optical lens of claim 15 wherein said lens body center area defines the light transmitting path to have a diameter which is less than the diameter of the lens body.

* * * * *